(12) United States Patent
Decewicz et al.

(10) Patent No.: US 12,350,509 B2
(45) Date of Patent: Jul. 8, 2025

(54) METHOD AND DEVICE FOR MICRO-STRUCTURING LIQUIDS, INCLUDING BODY FLUIDS

(71) Applicant: Plasma Investment Sp. z o.o, Wrocław (PL)

(72) Inventors: Sławomir Decewicz, Wrocław (PL); Sławomir Adamski, Jawor (PL); Bartłomiej Paszkiewicz, Wrocław (PL); Rafał Blum, Wrocław (PL); Edward Reszke, Wrocław (PL); Ihar Yelkin, Wrocław (PL)

( * ) Notice: Subject to any disclaimer, the term of this patent is extended or adjusted under 35 U.S.C. 154(b) by 1049 days.

(21) Appl. No.: 17/293,759

(22) PCT Filed: Nov. 12, 2019

(86) PCT No.: PCT/PL2019/000102
§ 371 (c)(1),
(2) Date: May 13, 2021

(87) PCT Pub. No.: WO2020/101513
PCT Pub. Date: May 22, 2020

(65) Prior Publication Data
US 2022/0176139 A1    Jun. 9, 2022

(30) Foreign Application Priority Data
Nov. 16, 2018    (PL) ...................... P.427800

(51) Int. Cl.
*A61N 1/40*    (2006.01)
*A61N 2/00*    (2006.01)
*A61N 2/02*    (2006.01)

(52) U.S. Cl.
CPC ............... *A61N 1/40* (2013.01); *A61N 2/004* (2013.01); *A61N 2/02* (2013.01)

(58) Field of Classification Search
CPC . A61N 1/40; A61N 2/004; A61N 2/02; A61N 2/00
See application file for complete search history.

(56) References Cited

FOREIGN PATENT DOCUMENTS

WO    WO-2017024196 A2 *   2/2017   ............ B01D 17/06

OTHER PUBLICATIONS

"What is a water cluster?" video retrieved from https://www.google.com/search?q=structure+of+water+claster&client=firefox-b-e&sca_esv=1b7c8f5127465da7&sxsrf=ADLYWIJe32HAIRx8XNaRidwGyF38bILU8g:1725265595333&ei=u3bVZqWGF Lirxc8P1J2smAc&start=10&sa=N&sstk=AagrsujfctZU8R8LGckgdHbo55lyk1p3lgC9U1dlXgEzF-qjHhq3ISMAETm9vEActxElm9b7BR_3JWerJuTarZOC2kX5kuSsJvWREQ&ved=2ahUKEwjlz8-.
(Continued)

*Primary Examiner* — Carrie R Dorna
*Assistant Examiner* — Joshua Daryl D Lannu
(74) *Attorney, Agent, or Firm* — Haukaas Fortius PLLC; Michael Haukaas; Paul K. Judd

(57) ABSTRACT

The subject of the invention is a method and device for micro-structuring liquids, including body fluids. The method consists in that the treated liquid exposes to the broadband noise electric and/or magnetic fields generated in the near zone by the broadband source of electrical and/or magnetic noise, with frequencies in the range from 100 Hz to 50 MHz in the form of densely packed strips appearing similar to noise. Device has a broadband source of electrical and/or magnetic noise connected to a current source (ZRI) equipped with a modulator (MOD) of amplitude and frequency of the power signal.

20 Claims, 8 Drawing Sheets

(56) References Cited

OTHER PUBLICATIONS

Figure 1:
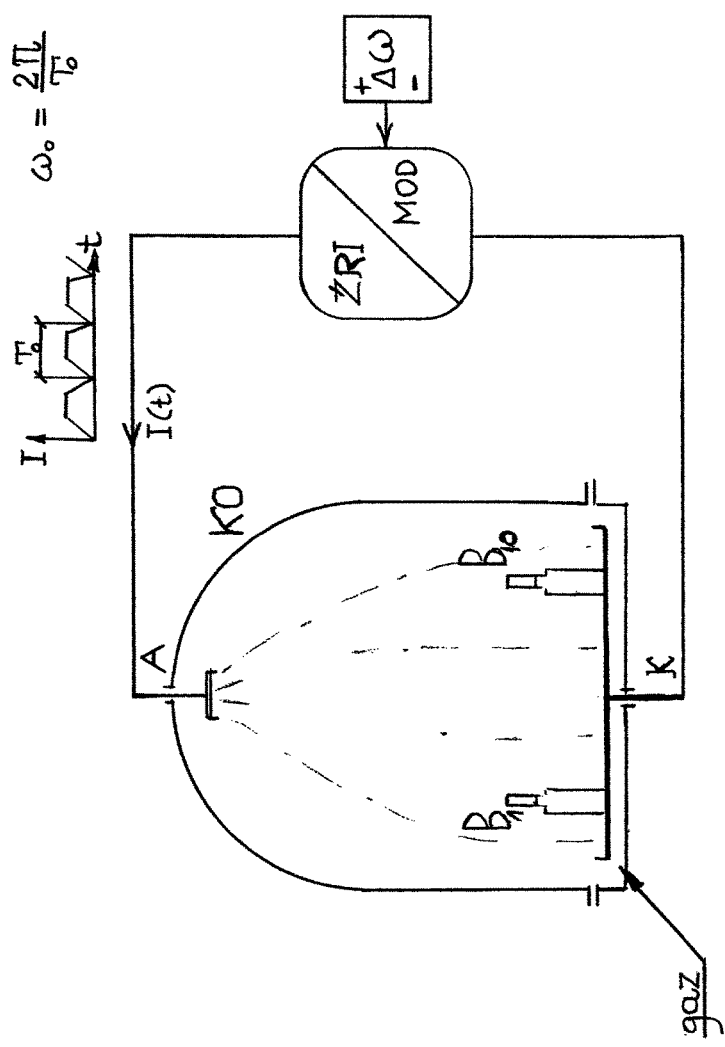

Azoulay, Jacob., "Memory features of water cyclically treated with magnetic field," World Journal of Engineering, vol. 13 No. 2, pp. 120-123, Apr. 2016.

Ball, Philip., "The memory of water," Nature., Oct. 8, 2004. doi:10.1038/news041004-19.

Brini et al., "How Water's Properties Are Encoded in Its Molecular Structure and Energies," Chem. Rev. 2017, 117, 12385-12414, Sep. 2017.

Chaplin, Martin F., "The Memory of Water: an overview," Homeopathy., 96(03): 143-150, Jul. 2007.

Enserink, Martin., "UNESCO to host meeting on controversial 'memory of water' research," Retrieved from http://www.sciencemag.org/news/2014/09/unesco-host-meeting-controversial-memory-water-research, Article date Sep. 23, 2014.

Ignatov et al., "Structure of water for origin of life and living matter," терИнтен журнал Науведение (15) (2013).

Kim et al., "Maxima in the thermodynamic response and correlation functions of deeply supercooled water," Science., 358, 1589-1593, Dec. 2017.

Kontogeorgis et al., "Water structure, properties and some applications—A review," Chemical Thermodynamics and Thermal Analysis., vol. 6, 100053, Jun. 2022.

Kulkarni et al., "Quantum chemical and electrostatic studies of anionic water clusters(H2O)n-," Journal of Molecular Structure: Theochem. 851 (1-3): 213, Abstract, Feb. 2008.

Ludwig, Ralf., "Water: From Clusters to the Bulk," Angew. Chem. Int. Ed. 40 (10): 1808-1827, Abstract, May 2001.

Maheshwary et al., "Structure and Stability of Water Clusters (H2O)n, n = 8-20". Journal of Physical Chemistry A. 105: 10525-10537, Abstract, Oct. 2001.

Meessen, Auguste., "Water Memory Due to Chains of Nano-Pearls," Journal of Modern Physics., 9, 2657-2724, Jan. 2018.

Montagnier et al., "DNA waves and water," J. Phys.: Conf. Ser. 306 012007, Dec. 2010.

Peltz et al., "Microstructure of Water At the Level of Three-particle Correlation Functions As Predicted by Classical Intermolecular Models," Molecular Simulation, 29(1), 13-21, Abstract, Oct. 2010.

Yang et al., "Ring-Stacking Water Clusters: Morphology and Stabilities," ChemistryOpen 2019, 8, 210-218, Feb. 2019.

Yelkin et al., "The Industrial Production of Water Dedicated to Absorption of Gases," Journal of Water Resource and Protection., 13, 632-653, Aug. 2021.

\* cited by examiner

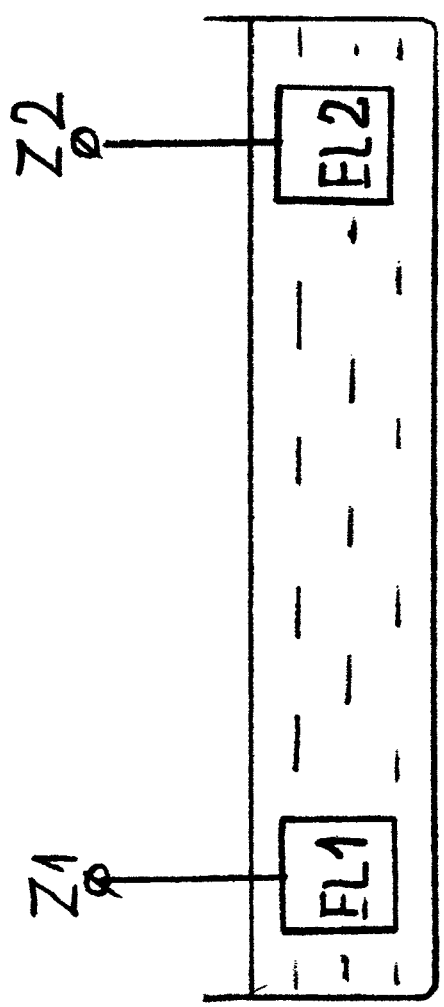

METHOD AND DEVICE FOR MICRO-STRUCTURING LIQUIDS, INCLUDING BODY FLUIDS

CROSS-REFERENCE TO RELATED APPLICATIONS

This application is a National Stage filing under 35 U.S.C. § 371 of International Application No. PCT/PL2019/000102, filed Nov. 12, 2019, which claims the benefit of Polish Patent Application No. P.427800 filed Nov. 16, 2018, which applications are incorporated herein by reference.

The subject of the invention is a method and device for micro-structuring liquids, including body fluids.

A device that generates electromagnetism with adjustable frequency bands and a method for generating electromagnetism is known from Chinese patent CN104274908 that provides a pulsating electromagnetic field for a biological effect and involves spectral analysis and quantum mechanics, and the biological effect of the pulsating electromagnetic field is obtained by quantitative calculations on theoretical basis. The device generating electromagnetism consists mainly of the white noise generator module, filtration module, gain control module, power amplification module and magnetic field generating module generates resonant frequency bands containing the main nucleons $^1H$, $^{13}C$, $^{14}N$, $^{17}O$, $^{23}Na$ and $^{31}P$ in organisms, and it sends a pulsating electromagnetic field with a variable frequency range, depending on the needs, and is of great importance for conducting experiments on animals and cell research experiments and illustrating the mechanism of biological action of the pulsating electromagnetic field during serving as a platform.

The method and the material processing device known from European patent application No. EP1674153 are used to convert entropy into anti-entropy by means of white electromagnetic noise that simulates natural or cosmic noise and is emitted more intensely than the natural protoplast. To simulate a natural protoplast, the emissions must be complex, double-polarized, clockwise and counter-clockwise, negative and positive. The implementation of this method is achieved by means of two white electromagnetic noise generators, in which one generator supplies a special broadband counterclockwise antenna, while the other supplies the identical, but consistent with the direction of the broadband antenna. This complex emission creates a double whirl that complements the information and organizes the disordered structure of the matter surrounding the device. The result is the elimination of all toxicity from the matter and the improvement of the biological and biotic level of all biological, non-parasitic, plant and animal organisms, releasing them from all kinds and forms of the disease.

The method of therapeutic interaction on cells and cell structures known from DE102004026074 is characterized in that the tissue containing these cells and cell structures is exposed to a weak quasi-electrostatic field whose frequencies represent "white noise" in the frequency range from 1 Hz up to several 100 GHz, which is emitted by a biologically active substance or living organism (biological modulator) and contains information on this substance or organism. The biological modulator has direct contact with the therapeutic facility.

The essence of the method according to the present invention is that the treated liquid exposes to the broadband noise electric and/or magnetic fields generated in the near zone by the broadband source of electrical and/or magnetic noise, with frequencies in the range from 100 Hz to 50 MHz in the form of densely packed strips appearing similar to noise.

Preferably, the broadband noise electric and magnetic fields are generated in the area of the low temperature plasma generated in the metal plasma chamber, wherein ultraviolet, visible and infrared radiation are treated only as a side effect of the plasma.

Preferably, a treated liquid contained in sealed dielectric liquid containers is placed inside a metal plasma chamber and exposed to broadband noise of electrical and magnetic field.

Preferably, the treated liquid is sealed in non-transparent dielectric liquid containers.

Preferably, broadband noise electric and magnetic fields are generated in the area of a low temperature plasma produced in at least one discharge lamp whose side walls are made of a dielectric material, wherein ultraviolet, visible and infrared radiation are treated only as a side effect of the plasma.

Preferably, the discharge lamp is placed close to the liquid to be treated, which is subjected to exposure to broadband noise electrical and magnetic field.

Preferably, the side walls of the discharge lamp are made of a dielectric material.

Preferably, the side walls of the discharge lamp are made of non-transparent dielectric material.

Preferably, a dielectric screen, preferably a non-transparent dielectric screen, is placed between the at least one discharge lamp and the liquid to be treated.

Preferably, at least one discharge lamp is placed close to the processed body or fluid of the living body which is subjected to exposure to broadband noise electrical and magnetic fields.

The essence of the device according to the invention lies in the microstructuring of liquids, including body fluids, characterized in that it has a broadband source of electrical and/or magnetic noise connected to a power source equipped with an amplitude and frequency modulator of the power supply signal.

Preferably, the broadband source of electrical and magnetic noise is a metal plasma chamber equipped with an anode and a cathode and connected to a gas source in which at least one dielectric liquid treatment container is located, preferably a bottle.

Preferably, a dielectric tank with a treated liquid made of non-transparent material.

Preferably, the broadband noise source is a noise reference lamp that is connected to the terminal by a power amplifier, most preferably a capacitor and adder are connected in series between the noise standard lamp and the power amplifier, wherein the broadband noise source output is connected to an applicator selected from the group: electrode applicator, optical applicator and an electric or magnetic applicator.

Preferably, the noise reference lamp is a noise Zener diode.

Preferably, the optical applicator is at least one coherent light source, most preferably an LED matrix.

Preferably, the electrode applicator is a system of at least two electrodes.

Preferably, the electric applicator is at least one electric dipole, preferably a dipole matrix.

Preferably, the electric applicator is at least one magnetic antenna, preferably a matrix of magnetic antennas.

Preferably, the broadband magnetic noise source is a noise standard lamp that is connected to the output terminal by a power amplifier. Preferably, a capacitor and an adder are connected in series between the noise standard lamp and the power amplifier, wherein the output of the broadband source of electric noise being connected to a magnetic applicator which constitutes at least one magnetic antenna, preferably a matrix of magnetic antennas.

Preferably, the noise reference lamp is a noise Zener diode. The method of micro-structuring liquids, including body fluids according to the invention, consisting in the effect of broadband electric and magnetic field in the near zone in the low frequency range as well as radio frequencies, does not generate free radicals in liquids or body fluids. In the present method, the transmission of energy between the broadband source of electrical and magnetic noise as well as the liquid and body fluid has a resonant character. The optical energy portion generated by the broadband noise source and characterized by high quantum energy values in the UV radiation range is eliminated by using screens or by using polarized LED light sources emitting below the UV area, which also eliminates this cause of ionization of gases. Thus the share of UV radiation in liquid microclastration processes has been completely eliminated.

The impact of broadband electric and magnetic field in the waveform of the low and high frequencies is characterized by the energy of quanta many orders lower than light quanta within the entire range from infrared to ultraviolet radiation. This range of light frequencies is usually associated with therapeutic lamps, solariums, etc. The broadband noise electric and magnetic fields generated in the low temperature plasma can be modified by selecting such plasma composition so that the noise correlates with hydrogen H oscillations in atomic lines as well as molecular ones, like e.g. in the OH bands. It gives it a "color" to the oscillations emitted by the discharge lamp in the form of broadband noise. It is necessary to emphasize the relatively high spectral energy density along the frequency spectrum, which creates very unique physical conditions when the system can associate a large amount of energy in the form of dense fringe or quasi-white noise, which does not change the amplitude in the working band. The levels of electric and magnetic field strength or electromagnetic field measured in the near-working zone of the 100 Hz-50 MHz frequency range are smaller than those acceptable for people exposed to continuous exposure. This allows the use of broadband sources of electrical and magnetic noise in the form of therapeutic devices such as beds or armchairs without restrictions i.e. in the mode defined as "wellness". The omitting to use the light emitted by the discharge lamps allows the treated persons to be clothed in their own clothes. Consequently, when processing liquids, they can remain in their original dielectric containers, even if the vessel walls are opaque or non-transparent. The possibility of the above-mentioned "staining" of the spectrum allows the use of the noise standard lamp as the reference source of the electrical signal produced in the circuit of the reference lamp, and then the use of appropriate applicators to transfer this signal as a magnetic or light electrical wave. This also creates new conditions for the use of electrodes to transfer these signals. In the case of a signal processed into a light wave, it is possible to use coherized LED light sources as well as semiconductor lasers. For partial coherence of light sources, it is worth to choose the wavelength of certain colors so that they coincide with the wavelengths of, for example, the Balmer series of the hydrogen atom, alternatively correspond to the frequency of the hydrogen molecules or e.g. the OH hydroxyl group. Comparison of the discharge lamp as an electric and magnetic antenna with electric and magnetic antennas made of metal electric conductors, leads to the conclusion that plasma as a source of radiation may have the advantage that the whole section of the plasma takes part in the field generation, whereas in metal conductors the current is focused only at the surface of the metal and its intensity is a function of frequency. The volume nature of the current in plasma with a small conductivity fully penetrated by the field allows to expect a significant broadband. In addition, the impedance range varies, which in systems with conductors usually ranges from 50 Ohm up to 377 Ohm free impedance. In the plasma of the discharge lamp, this impedance can, for example, reach 100 kOhm, which creates unique possibilities of achieving high efficiency of broadband energy radiations, unattainable for metallic antennas.

Figure 2:
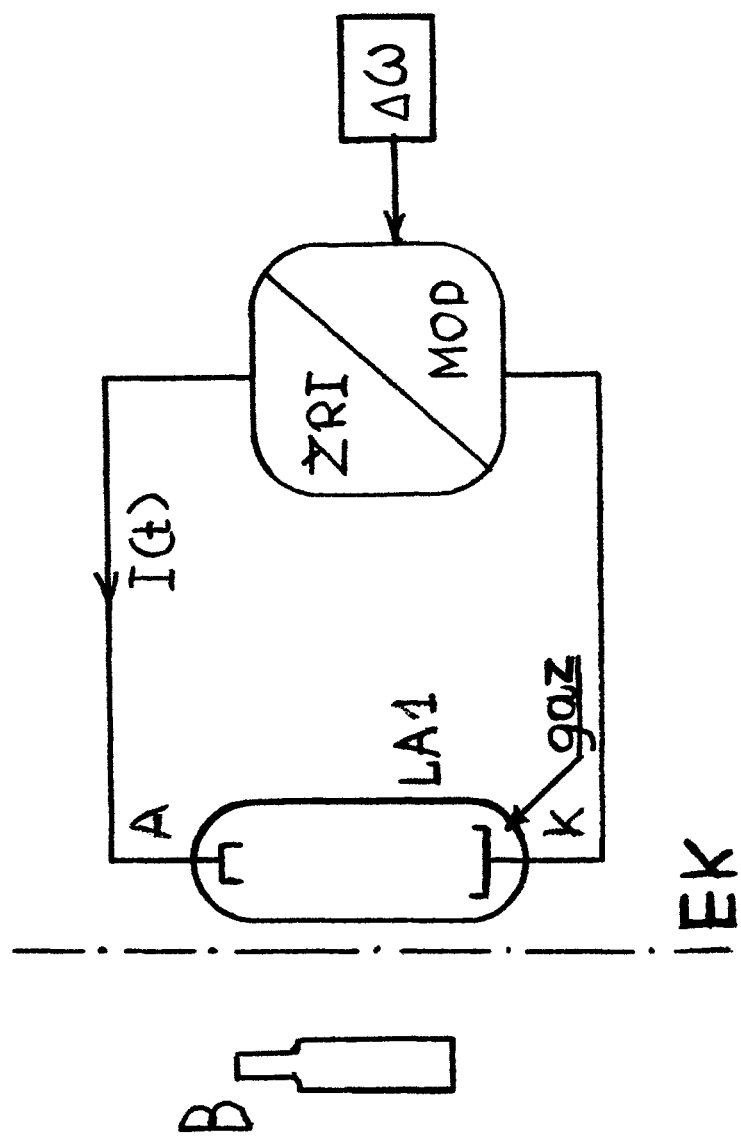
Figure 3:
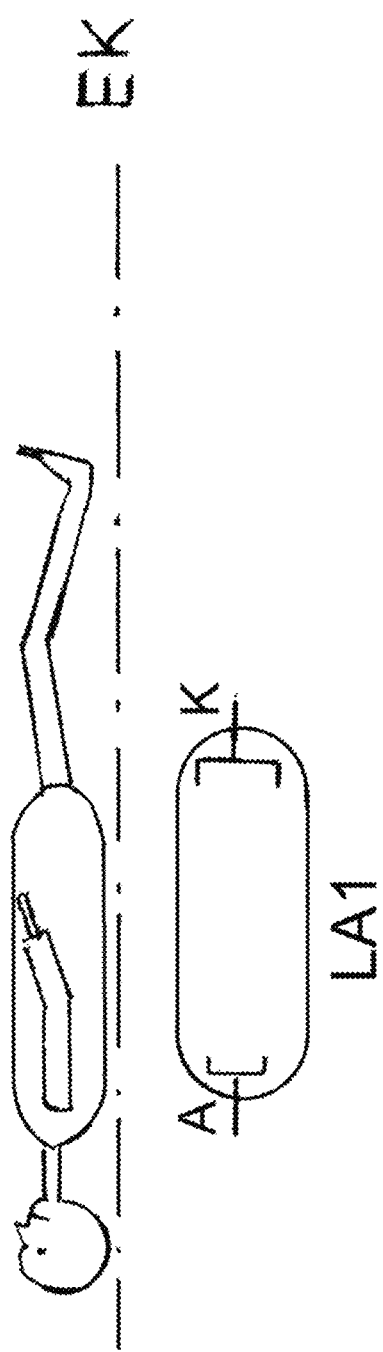
Figure 4:
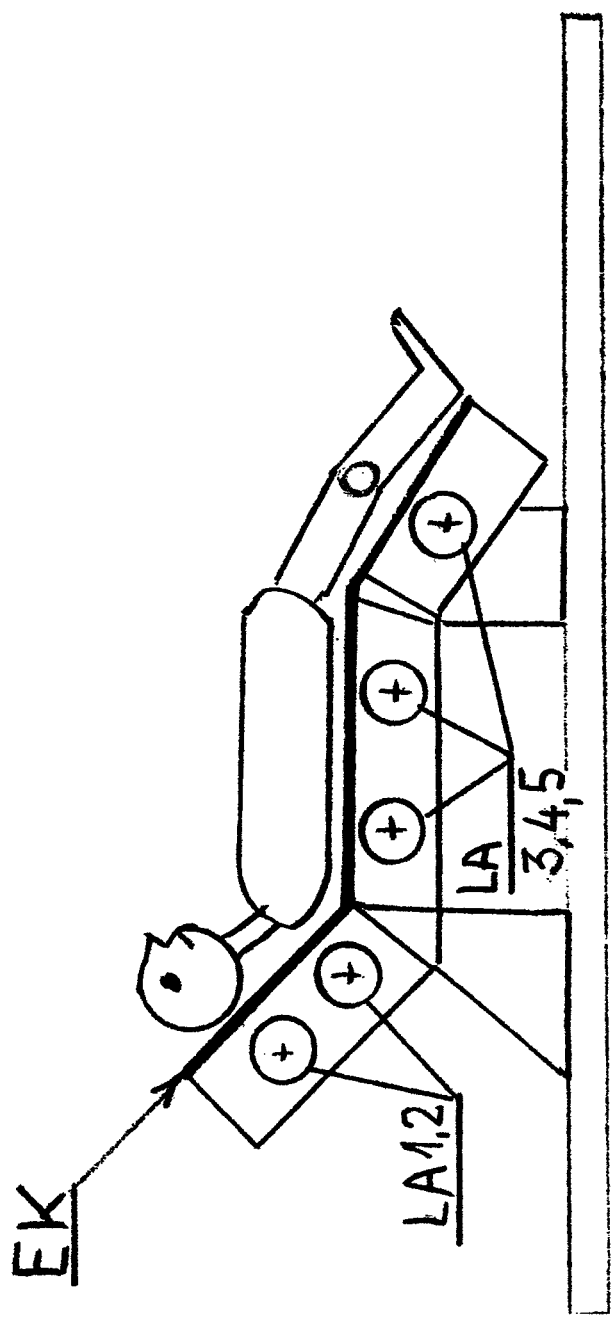
Figure 5:
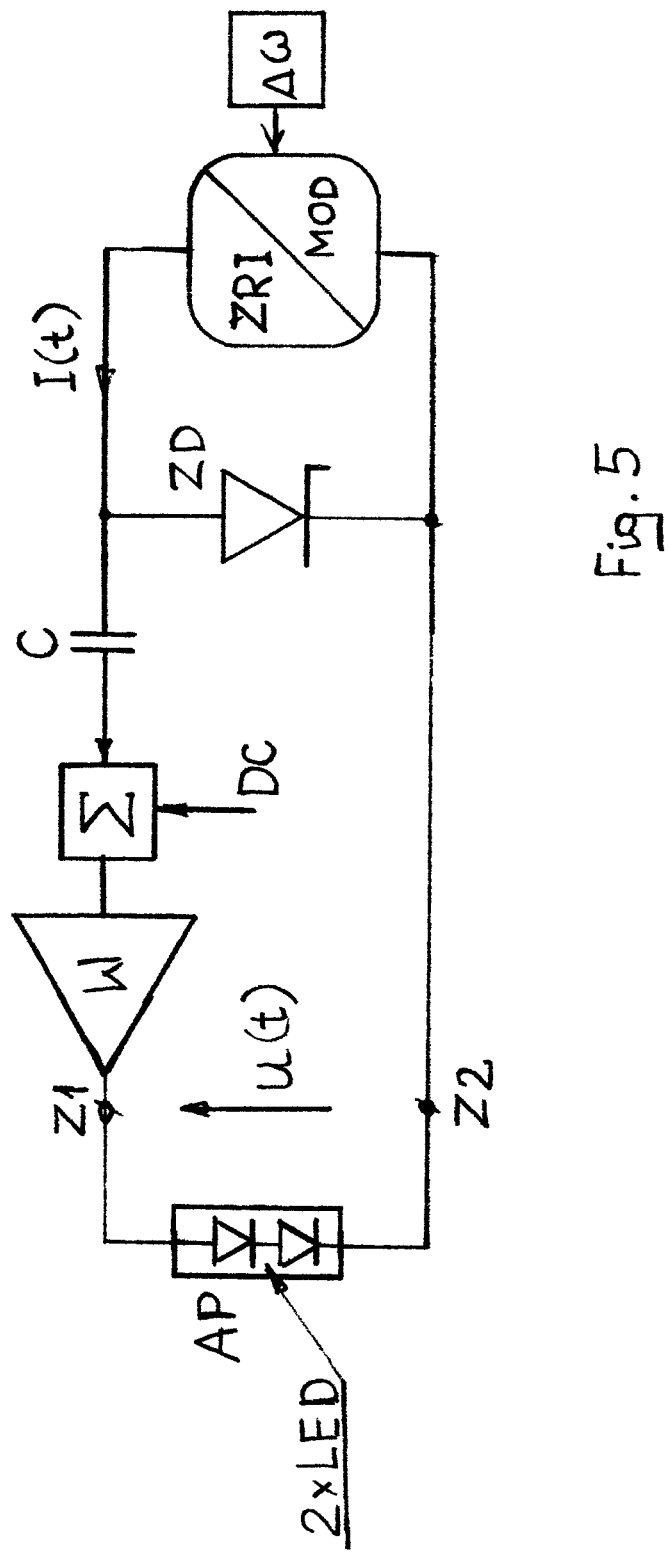
Figure 6:
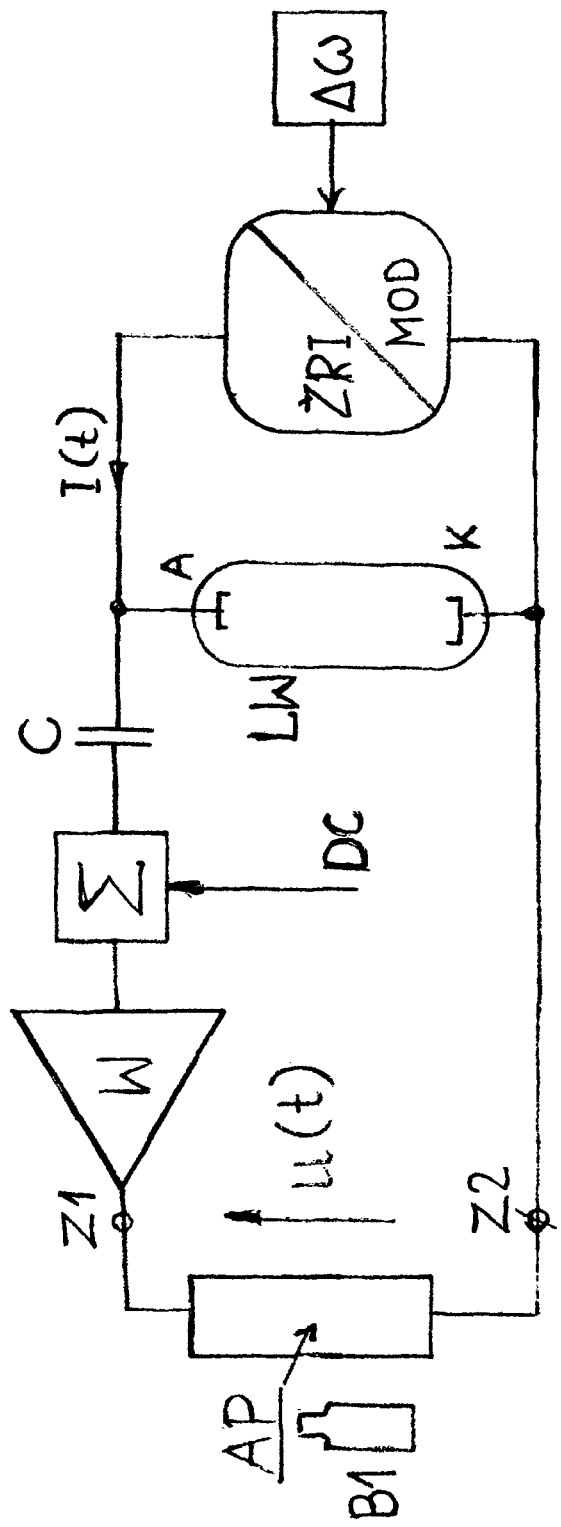
Figure 6A:
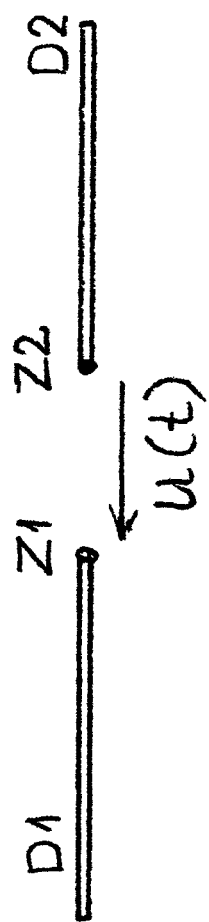
Figure 6B:

Objects of the inventions are explained in the embodiments and shown in the drawing, in which FIG. 1 shows a device for micro-structuring a liquid with a metal plasma chamber, FIG. 2—device for micro-structuring a liquid with one discharge lamp, FIG. 3—a micro-device for micro-structuring a liquid with one discharge lamp, FIG. 4—device for micro-structuring body fluids with five discharge lamps, FIG. 5—device for micro-structuring a liquid with an electric noise source comprising a Zener diode, FIG. 6—a micro-device structure of a liquid with an electric noise source using a noise standard lamp, FIG. 6a—an electric applicator with two electrical dipoles, FIG. 6b—a magnetic applicator with one magnetic antenna, and FIG. 6c—an electrode applicator with two electrodes.

EXAMPLE 1

The method of micro-structuring of liquids, including body fluids, consists in the fact that the treated liquid exposes to the operation of the broadband electric and magnetic field generated in the near zone by the broadband source of electrical and magnetic noise, with frequencies in the range from 100 Hz to 50 MHz having the form of densely packed stripes with a character similar to noise. The broadband electric and magnetic field is generated within the volume of low-temperature plasma generated in the metal plasma chamber KO, while ultraviolet, while visible and infrared radiation are treated only as a side effect of the plasma. In the metal plasma chamber KO, the treated liquid is enclosed in sealed dielectric liquid containers B1, B2, . . . , B10 in the form of, non-transparent tanks, and then exposed to the broadband electric and magnetic field. In addition, densely packed noise-like bands are generated by frequency modulation of the fundamental frequency of low-frequency pulsed signal supplying the anode A and the cathode K of the metal plasma chamber KO or the discharge lamp LA1.

EXAMPLE 2

The method of micro-structuring liquids, including body fluids, proceeds as in the first example, with the difference that the treated liquid is sealed in leak-proof dielectric liquid containers B1, B2, . . . , B10, the treated liquid being a saline placed in transparent glass bottles.

EXAMPLE 3

The method of micro-structuring liquids, including body fluids, proceeds as in the first or second example with the difference that the broadband electric and magnetic field is generated in the low temperature plasma produced in one discharge lamp LA1, whose side walls are made of a dielectric material, whereas ultraviolet, visible and infrared radiation is treated only as a side effect of the plasma, and the LA1 discharge lamp is placed close to the treated liquid, which is exposed to the broadband electric and magnetic field. The side walls of the LA1 discharge lamp are made of a transparent dielectric material. In addition, densely packed bands of the character similar to noise are generated by the frequency modulation of the fundamental frequency of the low frequency pulsed signal supplying the discharge lamp LA1.

EXAMPLE 4

The method of micro-structuring liquids, including body fluids, proceeds as in the third example, with the difference that the side walls of the discharge lamp LA1 are made of non-transparent dielectric material.

EXAMPLE 5

The method of micro-structuring liquids, including body fluids, proceeds as in the third example, with the difference that between the discharge lamp LA1 and the treated liquid a transparent dielectric screen EK is placed.

EXAMPLE 6

The method of micro-structuring liquids, including body fluids, proceeds as in the third example, with the difference that the LA1 discharge lamp is placed close to the processed body fluid of the living organism which is exposed to broadband noise electrical and magnetic field. The LA1 discharge lamp is embedded in the surface layer of the therapeutic furniture in the form of a table covered with a transparent EK dielectric screen. In addition, the modulator MOD of the amplitude and frequency of the signal is adjusted and one can monitor the amplitudes of the electric and magnetic fields to levels below the acceptable daily exposure standards for these electromagnetic fields.

EXAMPLE 7

The method of micro-structuring liquids, including body fluids, proceeds as in the sixth example, with the difference that the processed body fluid of the living organism is exposed to broadband noise electric and magnetic field, which are generated by means of five discharge lamps LA1, LA2, . . . , LA, which fits into the surface layer of the seat covered with a non-transparent EK dielectric screen, transmitting electromagnetic waves and microwaves, impermeable to light.

EXAMPLE 8

The method of micro-structuring of liquids, including body fluids, proceeds as in the first example with the difference that the broadband noise electric field is generated in the Zener diode ZD noise source, from which the noise electrical signal is added in the adder Σ to the signal source of the constant component DC, then the summed signal amplifies in the power amplifier W and it is powered by an electric applicator AP that generates a broadband noise electric field.

EXAMPLE 9

The method of micro-structuring of liquids, including body fluids, proceeds as in the first example with the difference that broadband noise electrical and magnetic field is generated in the area of low-temperature plasma in the standard noise lamp LW from which an electric noise signal is added to the DC component and so summed signal amplified in amplifier W feeds an optical applicator AP which radiates a broadband noise optical field.

EXAMPLE 10

The method of micro-structuring liquids, including body fluids, proceeds as in the eighth or ninth example with the difference that the signal is added together in the power amplifier W and supplied to the magnetic applicator AP, which generates a broadband noise magnetic field.

EXAMPLE 11

The device for the micro-structuring of liquids, including body fluids, has a broadband source of electrical and/or magnetic noise connected to the source of current AR equipped with an amplitude and frequency modulator MOD of the signal. The broadband source of electrical and magnetic noise is a metal plasma chamber KO equipped with anode A and cathode K and connected to a gas source. Plasma chamber KO is powered from amplitude and frequency modulated source at the angular frequency modulation depth $\Delta\omega$ modulator of amplitude and frequency MOD and pulsating current I(t), the angular frequency of ripple $\omega$ is $2\pi/T_o$, where $T_o$ is a period of the current ripples. In the plasma chamber KO there are placed ten dielectric containers with treated liquid made of transparent material, which are bottles B1, B2, . . . , B10.

EXAMPLE 12

Device for micro-structuring liquids, including body fluids made as in eleventh example, with the difference that the broadband source of electrical and magnetic noise is discharge lamp LA1 equipped with anode A and cathode K, near which the treated liquid B1 is placed enclosed in dielectric tank. The LA1 discharge lamp is supplied by the current I(t) delivered from the amplitude modulated source ZRI which is modulated in the amplitude and frequency, to the depth of $\Delta\omega$, in the amplitude and frequency modulator MOD. In addition, between the LA1 discharge lamp and the liquid being processed, there is placed a dielectric screen EK made of a non-transparent material, transmitting radio electromagnetic waves and microwaves, impermeable to light.

EXAMPLE 13

Device for micro-structuring liquids, including body fluids as in eleventh or twelfth example except that the treated liquid are body fluids exposed on a non-transparent dielectric screen EK, the LA1 discharge lamp is embedded in the surface layer of the therapeutic furniture in the form of a table covered with a transparent dielectric screen EK.

EXAMPLE 14

Device for micro-structuring liquids, including body fluids made as in the thirteenth example, with the difference that it has five discharge lamps LA1, LA2, . . . , LA, which incorporate the surface layer of the seat covered with a non-transparent dielectric screen EK.

EXAMPLE 15

Device for micro-structuring liquids, including body fluids made as in eleventh example, with the difference that the broadband source of electrical noise is the a standard noise lamp LW, which is connected to the first terminal Z1 through the power amplifier W. Between the standard noise lamp LW and the amplifier W capacitor C is connected in series with adder Σ input. At the output of broadband source of electrical noise there are the first terminals Z1 and the second Z2 to which the optical applicator AP is connected in the form of two polarized LED light sources, where polarized LED light sources emit light similar to the Balmer series of hydrogen lines: 656.28 nm pink line and the blue line at 486.18 nm.

EXAMPLE 16

Device for micro-structuring liquids, including body fluids made as in the fifteenth example with the difference that the broadband source of electrical noise is an electrode applicator AP, which is a system of two electrodes EL1, EL2.

EXAMPLE 17

Device for micro-structuring liquids, including body fluids made as in the fifteenth example with the difference that the broadband source of electrical noise is an electric applicator AP, which is a system of two electric dipoles D1, D2, supplied with noise voltage u (t).

EXAMPLE 18

Device for micro-structuring liquids, including body fluids made as in the fifteenth example with the difference that the broadband source of electrical noise constitutes the Zener noise diode ZD.

EXAMPLE 19

Device for micro-structuring liquids, including body fluids made as in eleventh example with the difference that the broadband source of magnetic noise is the noise standard lamp LW, which is connected to terminal Z1, Z2 through the power amplifier W. Between the noise standard lamp LW and the power amplifier W there are connected in series capacitor C and adder Σ. At the output of the broadband source of electrical noise are present the first terminals Z1 and the second Z2, to which the magnetic applicator AP is connected which constitutes a single magnetic antenna AM.

EXAMPLE 20

Device for micro-structuring liquids, including body fluids made as in the nineteenth example with the difference that the broadband source of electrical noise constitutes the Zener noise diode ZD.

Discharge lamps LA1, LA2, . . . , LA5, used as a broadband source of electrical and/or magnetic noise, can generate noise coherized with plasma gas dopant. If it is atmospheric air then there are many admixtures including water vapor. The broadband noise of electric and/or magnetic field generated in the discharge becomes a coherence noise. Further use of the generated broadband noise of electric and/or magnetic field, increase of its power or the surface from which it is emitted may involve multiplication of the number of discharge lamps LA1, LA2, . . . , LA5. Possible duplication of unit powers of LA1, LA2, . . . , LA5 discharge lamps, usually does not lead to good results, because for each construction there is an optimum power ensuring noise optimum. However, having a single LW reference lamp with optimized design, it may be used as a primary broadband source of electrical and/or magnetic noise, the signal of which can be amplified in broadband power amplifiers W, and then emitted for the appropriate radiating applicators AP. A suitably processed broadband noise and/or its magnetic field signal can be used to modulate the light of a polarized semiconductor LED light sources that can effectively interact with the liquid and body fluids. Continuing this thought regarding indirect broadband sources of electrical and/or magnetic noise, a commercial semiconductor white noise generator coherized by modulation with a coherent signal and resulting in a new coherized noise can be proposed. The use of light is nothing else but the use of an alternative path to transmit coherent noise information to the object OBJ being processed.

Noise reference lamp LW with glow plasma that generates light and electromagnetic field in the entire range of radio waves from long waves to VHF band, and with appropriate selection of DC supply voltage with DC component, one can generate white or quasi-white noise in a wide range of wavelengths.

LIST OF TERMS USED IN THE DRAWINGS

A—anode,
AM—magnetic antenna,
AP—radiating applicator,
B—dielectric vessel with liquid,
B1-B10—liquid container, set of bottles with liquid,
C—capacitor,
D1, D2—electric dipole,
DC—a source of constant electric current component,
EL1, EL2—electrode,
EK dielectric screen,
K—cathode,
KO—plasma chamber,
LW—standard noise lamp,
LA1, LA2, LA3, LA4, LA5—discharge lamp,
LED—semiconductor source of light,
MOD—amplitude and frequency modulator of the power signal,
OBJ—the object being processed,
Σ—adder,
W—power amplifier,
Z1, Z2—electric terminals,
ZD—Zener diode,
ZRI—current source,
I (t) pulsating current,
To—the period of current ripple,
$\omega = 2\pi/T_o$ is the angular frequency of the ripples,
Δω—angular modulation depth,
u (t)—the signal of the noise source.

The invention claimed is:

1. A method for micro-structuring liquids characterized in that a liquid to be treated is treated by exposing the liquid to a broadband noise of electrical and/or magnetic fields in a near zone generated by a broadband source of electrical and/or magnetic noise at frequencies in the range from 100 Hz to 50 MHz in a form of densely packed bands wherein the broadband noise of the electric and/or magnetic fields are generated in a low temperature plasma region produced in a metal plasma chamber (KO), thereby forming the treated liquid.

2. The method according to claim 1, characterized in that the liquid to be treated is placed in the metal chamber (KO)

containing closed liquid dielectric containers (BI-B10) and exposed to the broadband noise of the electrical and/or magnetic field.

3. The method according to claim 2, characterized in that the treated liquid is sealed in the dielectric liquid containers (B1-B10).

4. The method according to claim 1, wherein the broadband noise of electric and/or magnetic fields is generated in the low temperature plasma region produced in at least one discharge lamp (LAI, LA2, . . . , LA5), walls of which are produced from a dielectric material.

5. The method according to claim 4, characterized in that the at least one discharge lamp (LA1, LA2, . . . , LA5) is placed close to the liquid to be treated, which is subjected to exposure to the broadband noise of the electric and/or magnetic field.

6. The method according to claim 5, characterized in that side walls of the at least one discharge lamp (LA1, LA2, . . . , LA5) are made of a dielectric material.

7. The method according to claim 5, characterized in that side walls of the at least one discharge lamp (LA1, LA2, . . . , LA5) are made of non-transparent dielectric material.

8. The method according to claim 5, characterized in that between the at least one discharge lamp (LA1, LA2, . . . , LA5) and the liquid to be treated, a dielectric screen (EK) is placed.

9. The method according to claim 4, characterized in that at least one of the at least one discharge lamps (LA1, LA2, . . . , LA5) is placed close to a processed body fluid of a living organism and subjected to exposure to the broadband noise of the electric and/or magnetic field.

10. The method according to claim 9, wherein a body fluid treated in the living organism is exposed to at least one of the at least one discharge lamp (LA1, LA2, . . . , LA5), which is incorporated into a surface layer of therapeutic furniture wherein a modulator of amplitude and frequency of an input signal (MOD) regulates and monitors amplitudes of the electric and/or magnetic fields.

11. The method according to claim 1, characterized in that the densely packed bands are generated by a shallow frequency modulation of a fundamental frequency of a low-frequency pulsed signal supplying an anode (A) and a cathode (K) of the metal plasma chamber (KO) or discharge lamp (LA1, LA2, . . . , LA5).

12. The method according to claim 1, characterized in that the broadband noise of the electric and/or magnetic fields is generated in a junction area of a Zener noise diode (ZD) from which an electrical noise signal is added in an adder (L) to a DC source signal, then a summed signal is amplified in a power amplifier (W) and feeds applicator (AP), which generates a broadband noise field selected from the group of: electric field, magnetic field, or optical field.

13. The method according to claim 1, characterized in that the broadband noise of the electric and/or magnetic fields are generated in an area of low temperature plasma generated in a standard noise lamp (LW) from which an electrical noise signal is added in an adder (L) to a DC source signal, then a summed signal is amplified in a power amplifier (W) and feeds an applicator (AP), which generates the broadband noise selected from the group of: electric field, magnetic field, or optical field.

14. The method of claim 1, wherein the liquid to be treated comprises body fluids.

15. A device for micro-structuring liquids characterized in that the device has a broadband source of electrical and/or magnetic noise connected to a current source (ZRI) equipped with a modulator (MOD) of amplitude and frequency of a power signal characterized in that the broadband source of electrical and/or magnetic noise is a metal plasma chamber (KO) equipped with an anode (A) and cathode (K) and connected to a gas source in which at least one dielectric liquid treatment tank is located.

16. The device according to claim 15, characterized in that the broadband source of electrical and/or magnetic noise is at least one discharge lamp (LA1, LA2, . . . , LA5) equipped with the anode (A) and the cathode (K), near which a treated liquid is located.

17. The device according to claim 16, characterized in that the treated liquid is located in at least one dielectric container.

18. The device according to claim 15, characterized in that the broadband source of electrical and/or magnetic noise is a noise reference lamp (LW) which is connected to a terminal (Z1, Z2) via a power amplifier (W), between the noise reference lamp (LW) and the power amplifier (W) there are included capacitor (C) and adder (L) connected in series, hereby output of the broadband source of electrical and/or magnetic noise is connected to an applicator (AP) selected from the group of electrode applicator, optical applicator, and electric applicator.

19. The device according to claim 15, characterized in that the broadband source of electrical and/or magnetic noise is a noise reference lamp (LW) which is connected to a terminal (Z1, Z2) via a power amplifier (W), between the noise reference lamp (LW) and the power amplifier (W) there are included capacitor (C) and adder (L) connected in series, wherein an output of the broadband source of electrical and/or magnetic noise is connected to a magnetic applicator (AP) which constitutes at least one magnetic antenna (AM).

20. The device of claim 15, wherein the liquid to be treated comprises body fluids.

* * * * *